(12) United States Patent
Murai et al.

(10) Patent No.: US 8,211,606 B2
(45) Date of Patent: Jul. 3, 2012

(54) COLORING COMPOUND, YELLOW TONER, SHEET FOR HEAT-SENSITIVE TRANSFER RECORDING, AND INK

(75) Inventors: Yasuaki Murai, Kawasaki (JP); Masashi Hirose, Machida (JP); Masayoshi Kato, Tokyo (JP); Takayuki Toyoda, Yokohama (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 310 days.

(21) Appl. No.: 12/180,252

(22) Filed: Jul. 25, 2008

(65) Prior Publication Data

US 2009/0075193 A1   Mar. 19, 2009

Related U.S. Application Data

(63) Continuation of application No. PCT/JP2008/055616, filed on Mar. 18, 2008.

(30) Foreign Application Priority Data

Mar. 19, 2007   (JP) .................................. 2007-070494

(51) Int. Cl.
*G03G 9/09* (2006.01)
(52) U.S. Cl. ................ 430/108.23; 106/31.47; 534/606; 534/612
(58) Field of Classification Search ............ 430/108.23; 534/606, 612; 106/31.48
See application file for complete search history.

(56) References Cited

U.S. PATENT DOCUMENTS

| | | | |
|---|---|---|---|
| 3,979,378 A | 9/1976 | Gnad et al. | 260/156 |
| 4,327,018 A * | 4/1982 | Liechti et al. | 534/604 |
| 4,668,774 A * | 5/1987 | Loeffler et al. | 106/31.48 |
| 4,734,349 A | 3/1988 | Chapman et al. | 430/106 |
| 4,968,657 A | 11/1990 | Gregory et al. | 503/227 |

(Continued)

FOREIGN PATENT DOCUMENTS

DE   2002022 A  *  7/1971

(Continued)

OTHER PUBLICATIONS

Diamond, Arthur S & David Weiss (eds.) Handbook of Imaging Materials, 2nd ed.. New York: Marcel-Dekker, Inc. (Nov. 2001) pp. 178-182.*

(Continued)

*Primary Examiner* — Christopher Rodee
(74) *Attorney, Agent, or Firm* — Fitzpatrick, Cella, Harper & Scinto (57) ABSTRACT

A coloring compound is provided which is excellent in coloring ability and transparency, has high solubility in organic solvents, and is superior in light resistance. A toner, a sheet for heat-sensitive transfer recording and an ink that use the coloring compound are also provided. The coloring compound is represented by the following general formula:

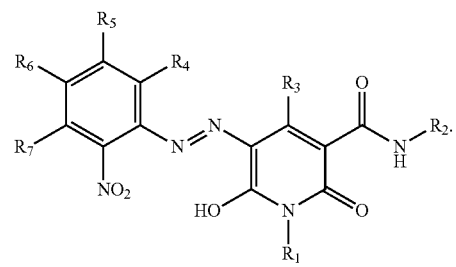

7 Claims, 2 Drawing Sheets

U.S. PATENT DOCUMENTS

| | | | |
|---|---|---|---|
| 2008/0069045 A1 | 3/2008 | Delamotte et al. | 370/330 |
| 2008/0220358 A1 | 9/2008 | Tanaka et al. | 430/108.23 |

FOREIGN PATENT DOCUMENTS

| | | |
|---|---|---|
| DE | 2004487 | 8/1971 |
| DE | 1360749 | 11/1972 |
| DE | 2162179 A * | 2/1975 |
| EP | 163113 A2 * | 12/1985 |
| GB | 2032448 | 5/1980 |
| JP | 48-056974 | 8/1973 |
| JP | 02-243395 | 9/1990 |
| JP | 03-042676 | 2/1991 |
| JP | 05-255602 | 10/1993 |
| JP | 05-331382 | 12/1993 |
| JP | 06-059510 | 3/1994 |
| JP | 08-110653 | 4/1996 |
| JP | 09-111143 | 4/1997 |
| JP | 11-314467 | 11/1999 |
| JP | 2000-062327 | 2/2000 |
| JP | 2000-239549 | 9/2000 |
| WO | WO 2008/069045 A1 | 6/2008 |

OTHER PUBLICATIONS

EPO machine translation of DE 2002022 (Jul. 1971).*
International Preliminary Report on Patentability of PCT/JP2008/055616 dated Sep. 22, 2009.

* cited by examiner

COLORING COMPOUND, YELLOW TONER, SHEET FOR HEAT-SENSITIVE TRANSFER RECORDING, AND INK

This application is a continuation of International Application No. PCT/JP2008/055616, filed on Mar. 18, 2008, which claims the benefit of Japanese Patent Application No. 2007-070494 filed on Mar. 19, 2007.

BACKGROUND OF THE INVENTION

1. Field of the Invention

The present invention relates to a new coloring compound, a yellow toner including the coloring compound, a sheet for heat-sensitive transfer recording having a coloring material layer including the coloring compound, and an ink including the coloring compound.

2. Description of the Related Art

With a change in lifestyle due to recent scientific and technological advances, dyes have become used not only in the conventional applications such as dyeing or coloring various materials including fibers, plastics and leathers, but also in a variety of industrial fields, taking advantage of their characteristics of recording or displaying information. Particularly, as personal computers have rapidly come into wide use in recent years, hard copy technologies typified by electrophotographic recording and heat-sensitive transfer recording have been advanced for recording the character and image information output therefrom.

The electrophotographic recording method generally involves: forming an electrical latent image of static charge on a photosensitive member including a photoconductive material by various means; developing the latent image with toner to make a powder image; transferring, as needed, the powder image to paper or the like; and then fixing the image by heating, pressurization, solvent vapor, or the like. In recent years, a method for obtaining a full color image has also been put to practical use, which involves performing exposure and latent image formation using dispersed light and developing the latent image with color toner. In addition, a digital full color copier or printer in which the electrophotographic process is digitized has gone into actual use, which has made it possible to achieve images excellent not only in resolution and gradation property but also in color reproducibility without irregular color. As a result, there is a need for development of colorants for toner good in color tone and excellent in light resistance.

With recent widespread use of digital cameras, home printing of photos has now come to prevail; printers using a heat-sensitive transfer recording system are now in increasing demand, which have advantages in that the image recorders thereof can be made small-sized and low-cost, operation and maintenance are easy, and running costs are low. The heat-sensitive transfer recording method involves superposing a heat-sensitive transfer recording sheet having a coloring material layer including a heat-transferable colorant on a sheet-like substrate and an image-receiving sheet having a dye-receiving layer on the surface and heating the heat-sensitive transfer recording sheet to transfer the colorant in the coloring material layer of the heat-sensitive transfer recording sheet to the image-receiving sheet for recording. In the heat-sensitive transfer recording method, the heat-sensitive transfer recording sheet and the colorant contained in the ink composition used in the heat-sensitive transfer recording sheet are very important because they have a large influence on the speed of transfer recording, the image quality and storage stability of recorded matter, and the like. Performances specifically required for the colorant used include spectral properties capable of realizing a preferable color reproduction range, compatibility between heat transferability and fixability after transfer, thermal stability, and various fastness properties of the resulting image.

Pyridone azo dyes and pigments are known as coloring compounds used as yellow colorants (for example, see patent documents 1 to 3). These pyridone azo dyes generally have large molar absorption coefficients, and the toners and heat-sensitive transfer recording sheets obtained using these coloring compounds as colorants have high coloring ability, clarity and coloring power.

Pigments such as C.I. Pigment Yellow 93 and C.I. Pigment Yellow 155 have conventionally been commonly used as yellow colorants for toner, but there has been a need for a further improvement in a color tone and compatibility with resin. To improve these characteristics, new pyridone azo dyes for toner have been studied. For example, patent documents 4 to 7 propose the use of oil-soluble pyridone azo dyes as yellow toner colorants for electrophotography. However, a further improvement has been desired for satisfying characteristics as a toner colorant, particularly all of the color tone, compatibility with resin and light resistance, at a high level.

Methine disperse dyes such as C.I. Disperse Yellow 201 or disazo disperse dyes such as C.I. Disperse Orange 13 has previously been used as yellow colorants employed for heat-sensitive transfer recording sheets. However, to further improve characteristics such as, particularly, a color tone, ink-forming properties (solvent solubility) and light resistance, new yellow colorants used for heat-sensitive transfer recording sheets are being studied. For example, patent documents 8 to 13 propose the use of pyridone azo coloring compounds as yellow colorants. Nevertheless, a further improvement has been desired for satisfying all of the above characteristics as a colorant for heat-sensitive transfer recording sheets at a high level.

Patent document 1: Japanese Patent Application Laid-Open No. H09-111143
Patent document 2: German Patent No. 2004487
Patent document 3: U.K. Patent No. 2032448
Patent document 4: Japanese Patent Application Laid-Open No. H03-042676
Patent document 5: Japanese Patent Application Laid-Open No. H06-059510
Patent document 6: Japanese Patent Application Laid-Open No. H08-110653
Patent document 7: U.S. Pat. No. 4,734,349
Patent document 8: U.S. Pat. No. 4,968,657
Patent document 9: Japanese Patent Application Laid-Open No. H05-255602
Patent document 10: Japanese Patent Application Laid-Open No. H05-331382
Patent document 11: Japanese Patent Application Laid-Open No. H11-314467
Patent document 12: Japanese Patent Application Laid-Open No. 2000-062327
Patent document 13: Japanese Patent Application Laid-Open No. 2000-239549

SUMMARY OF THE INVENTION

An object of the present invention is to provide a coloring compound that is excellent in coloring ability and transparency, has high solubility in organic solvents, and is superior in light resistance. Another object of the present invention is to provide a yellow toner that gives an image having a good color tone and excellent in storage stability when the coloring compound is used as a colorant for the toner. Still another object of the present invention is to provide a sheet for heat-sensitive transfer recording, which gives an image having a good color tone and excellent in storage stability when the coloring compound is used as a colorant contained in the coloring material layer of the sheet for heat-sensitive transfer recording. Yet another object of the present invention is to provide an ink that gives an image having a good color tone and excellent in storage stability when the coloring compound is used as a colorant for the ink.

The above objects are achieved by the present invention described below. Specifically, the present invention provides a coloring compound characterized by having a structure represented by the following general formula (1).

In the formula (1), $R_1$ represents a hydrogen atom, an optionally substituted alkyl group, an optionally substituted aryl group, or an optionally substituted aralkyl group; $R_2$ represents a hydrogen atom, an optionally substituted alkyl group, an optionally substituted cycloalkyl group, or an optionally substituted aralkyl group; $R_3$ represents an optionally substituted alkyl group, or an optionally substituted aryl group; the total number of carbon atoms of $R_1$, $R_2$ and $R_3$ is 4 or more; $R_4$, $R_5$ and $R_7$ each independently represent a hydrogen atom, or any substituent group; and $R_6$ represents a hydrogen atom, a fluorine atom, a trifluoromethyl group, or a cyano group.

The present invention also provides a toner, particularly a yellow toner, characterized in that the yellow toner has yellow toner particles including at least a binder resin and a colorant, wherein the colorant includes a coloring compound having a structure represented by the above general formula (1).

The present invention also provides a sheet for heat-sensitive transfer recording characterized by including a substrate and a coloring material layer containing a coloring compound having a structure represented by the above general formula (1) on the substrate.

The present invention also provides an ink characterized by including a coloring compound having a structure represented by the above general formula (1).

According to the present invention, a coloring compound is provided which is excellent in coloring ability and transparency, has high solubility in organic solvents, and is superior in light resistance. A yellow toner is also provided which gives an image having a good color tone and excellent in storage stability when the coloring compound is used as a colorant for the toner. A sheet for heat-sensitive transfer recording is also provided which gives an image having a good color tone and excellent in storage stability when the coloring compound is used as a colorant contained in the coloring material layer of the sheet for heat-sensitive transfer recording. An ink is also provided which gives an image having a good color tone and excellent in storage stability when the coloring compound is used as a colorant for the ink.

Further features of the present invention will become apparent from the following description of exemplary embodiments with reference to the attached drawings.

DESCRIPTION OF THE EMBODIMENTS

Figure 1:
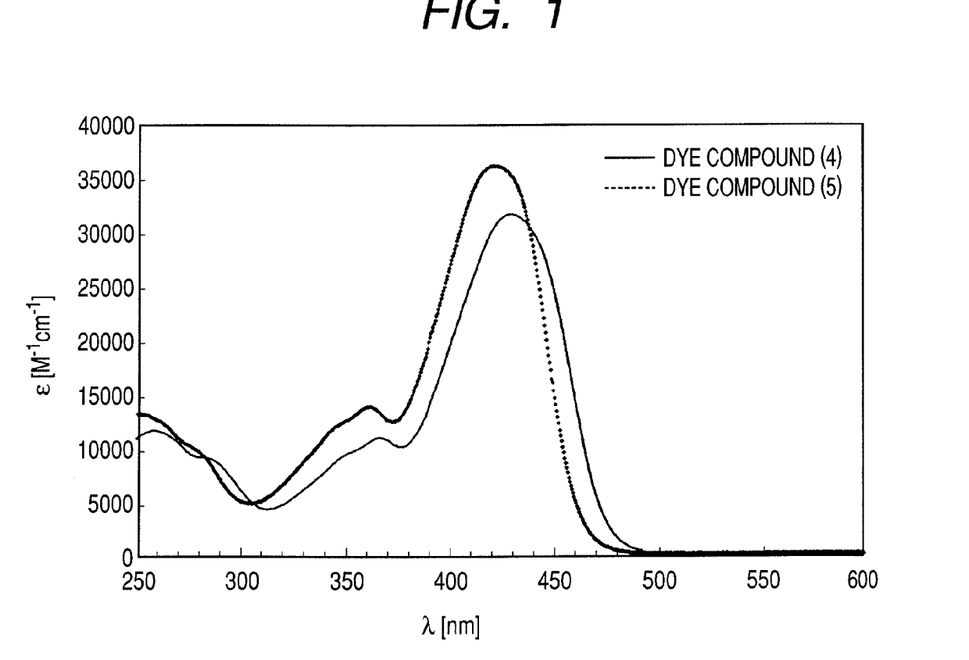
FIG. 1 is a graph illustrating the ultraviolet and visible absorption spectra of coloring compound (4) (solid line) and coloring compound (5) (broken line) according to the present invention at room temperature in methanol.
Figure 2:
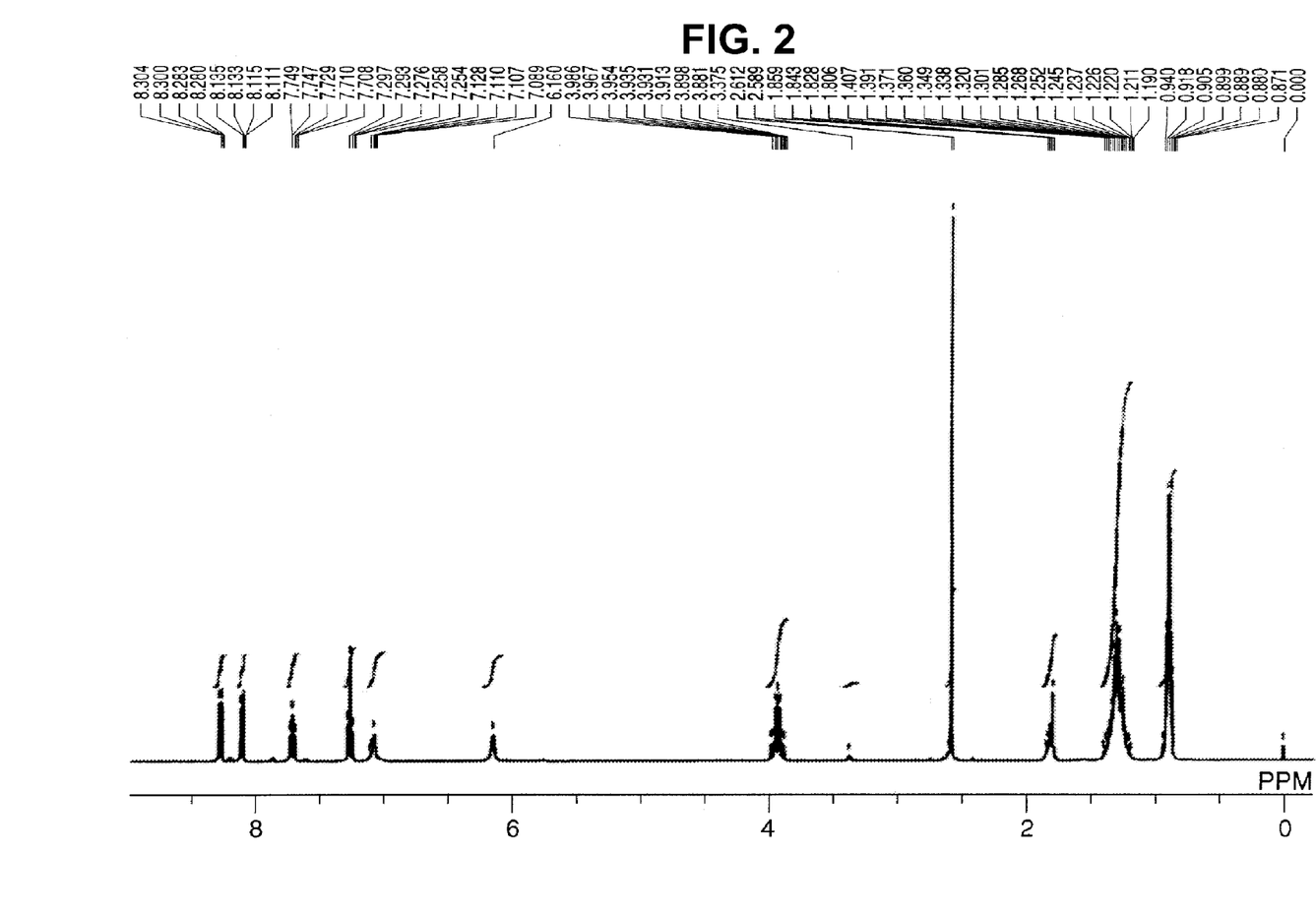
FIG. 2 is a graph illustrating the $^1$H NMR spectrum of the coloring compound (4) according to the present invention at room temperature in CDCl$_3$.

The present invention is described below in further detail by way of preferable embodiments thereof.

As a result of intensive studies for solving the above-described problems of the conventional techniques, the present inventors have found that a coloring compound having a structure represented by the formula (1) described below is excellent in coloring ability and transparency, has high solubility in organic solvents, particularly a nonpolar organic solvent, and is superior in light resistance, thereby accomplishing the present invention. It has further been found that the coloring compound is useful as a colorant for a yellow toner, as a colorant contained in the coloring material layer of a sheet for heat-sensitive transfer recording, and as a colorant for an ink, arriving at the present invention. The coloring compound having a structure represented by the following formula (1) is described below in detail.

In the formula (1), $R_1$ represents a hydrogen atom, an optionally substituted alkyl group, an optionally substituted aryl group, or an optionally substituted aralkyl group; $R_2$ represents a hydrogen atom, an optionally substituted alkyl group, an optionally substituted cycloalkyl group, or an optionally substituted aralkyl group; $R_3$ represents an optionally substituted alkyl group or an optionally substituted aryl group; the total number of carbon atoms of $R_1$, $R_2$ and $R_3$ is 4 or more; $R_4$, $R_5$ and $R_7$ each independently represent a hydrogen atom or any substituent group; and $R_6$ represents a hydrogen atom, a fluorine atom, a trifluoromethyl group, or a cyano group.

In the general formula (1), the alkyl groups for $R_1$ and $R_3$ are not particularly limited; however, they are each preferably a straight-chain alkyl group or a branched alkyl group. Examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, and a 2-ethylhexyl group.

In the general formula (1), $R_1$ and $R_3$ may each be an aryl group without particular limitation; examples thereof include a phenyl group and a naphthyl group.

In the general formula (1), $R_1$ may be an aralkyl group again without particular limitation; examples thereof include a benzyl group, a phenethyl group, and a phenylpropyl group.

In the general formula (1), $R_1$ and $R_3$ each independently represent a substituent as described above, and may be further substituted. Examples of the optional substituent group in this case include an alkyl group such as a methyl group, an ethyl group, and a tert-butyl group, a halogen atom, a nitro group, a carbamoyl group, an amide group, a sulfamoyl group, a sulfonamide group, and an alkoxy group.

The compound of the general formula (1) is preferably a compound in which $R_1$ is a hydrogen atom or an alkyl group and $R_3$ is a methyl group or a phenyl group in view of the availability of raw materials and the easiness of synthesis.

In the general formula (1), $R_2$ may be an alkyl group without particular limitation. However, it is preferably a straight-chain alkyl group or a branched alkyl group; examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, and a 2-ethylhexyl group.

In the general formula (1), $R_2$ may be a cycloalkyl group without particular limitation; examples thereof include a cyclopentyl group, a cyclohexyl group, and a cycloheptyl group. It may also be a cycloalkyl group whose carbon atoms are partly or wholly substituted with heteroatoms. Specific examples thereof include a tetrahydrofuryl group, a tetrahydropyranyl group, a pyrrolidinyl group, a piperazinyl group, and a morpholinyl group.

In the general formula (1), $R_2$ may be an aralkyl group without particular limitation; examples thereof include a benzyl group, a phenethyl group, and a phenylpropyl group.

In the general formula (1), $R_2$ represents a substituent as described above, and may be further substituted. Examples of the optional substituent group in this case include an alkyl group such as a methyl group, an ethyl group, and a tert-butyl group, a halogen atom, a nitro group, a carbamoyl group, an amide group, a sulfamoyl group, a sulfonamide group, and an alkoxy group.

The compound of the general formula (1) is preferably a compound in which $R_2$ is a hydrogen atom or an alkyl group having 3 or more carbons in view of the easiness of synthesis.

In the compound of the general formula (1), the substituents $R_1$, $R_2$, and $R_3$ are changed so that its solubility in a nonpolar solvent or an aqueous medium can be controlled. The total number of carbon atoms of $R_1$, $R_2$, and $R_3$ is required to be 4 or more in view of solubility in nonpolar solvents and compatibility with resin; at least one selected from the group consisting of $R_1$, $R_2$, and $R_3$ preferably represents a substituent having 4 or more carbons.

In the general formula (1), $R_4$, $R_5$, and $R_7$ each independently represent a hydrogen atom or any substituent group. Here, the "any substituent group" is not particularly limited; examples thereof include the following: an alkyl group, an alkoxy group, a halogen atom, a carbamoyl group, an amide group, a sulfamoyl group, a sulfonamide group, a hydroxyl group, a cyano group, a nitro group, and an alkyl ester group. In view of the color tone and light resistance, it is preferable that all of $R_4$, $R_5$, and $R_7$ are hydrogen atoms, or at least one of them is a halogen atom and the others are hydrogen atoms.

In the general formula (1), $R_6$ represents a hydrogen atom, a fluorine atom, a trifluoromethyl group, or a cyano group. In view of the color tone and light resistance, it is preferable that $R_6$ is a fluorine atom, a trifluoromethyl group, or a cyano group.

A method for producing the coloring compound having a structure represented by the above general formula (1) according to the present invention is described below. The method for producing the coloring compound having a structure represented by the above general formula (1) preferably includes the following step. That is, the method preferably includes the step of coupling a pyridone compound having a structure represented by the following general formula (2) with a diazo component of an aniline derivative having a structure represented by the following general formula (3).

General Formula (2)

In the general formula (2), $R_1$, $R_2$, and $R_3$ have the same meaning as $R_1$, $R_2$, and $R_3$ in the above-described general formula (1).

General Formula (3)

In the general formula (3), $R_4$, $R_5$, $R_6$, and $R_7$ have the same meaning as $R_4$, $R_5$, $R_6$, and $R_7$ in the above-described general formula (1).

According to the present invention, the above coupling step can be performed by a known diazo coupling method. For example, the coupling may be conducted by a method as described below. A sodium nitrite aqueous solution is first added to an aniline derivative having a structure represented by the above general formula (3) in hydrochloric acid to diazotize the aniline derivative according to the ordinary method. The diazotized derivative is then added to a solution of pyridones having a structure represented by the formula (2) to perform a coupling reaction. Further, the reaction solution is discharged into a poor solvent or the like, followed by filtering off the generated compound to produce a coloring compound having a structure represented by the above general formula (1). However, the coupling reaction is not limited thereto.

The coloring compound having a structure represented by the general formula (1), obtained by the above reaction, is treated according to a conventional method for after-treatment of organic synthesis reaction, and then purified. The resultant coloring compound was subjected to structural identification by $^1H$ and $^{13}C$ nuclear magnetic resonance spectrometric analysis (ECA-400 from JOEL Ltd.), ESI-TOF MS (LC/MSD TOF from Agilent Technologies), HPLC analysis (LC-20A from Shimadzu Corporation), and UV/Vis spectrometry (a U-3310-type spectrophotometer from Hitachi Ltd.).

The coloring compound according to the present invention has a bright yellow tone and can be used as a colorant, and preferably as a colorant for recording image information by virtue of its spectral properties. Specifically, the coloring compound can be used for toner, a sheet for heat-sensitive transfer recording, or ink, as detailed below. It is particularly preferably used as a colorant for toner or a colorant contained in the coloring material layer of a sheet for heat-sensitive transfer recording.

The yellow toner of the present invention will now be described.

The yellow toner of the present invention is characterized by using the coloring compound according to the present invention as a colorant.

The binder resin used in the yellow toner may be any binder resin generally employed in toners. Examples thereof include styrene resins, acrylic resins, styrene-acrylic resins, and polyester resins.

For the purpose of imparting improved flowability and charge controllability to the toner, at least one of inorganic fine particles and organic fine particles may be externally added to particles of the toner. Among these externally added fine particles, silica or titania fine particles are preferably used which is obtained by treating the surfaces of the fine particles with an alkyl group-containing coupling agent or the like. In this respect, these fine particles preferably have a number average primary particle diameter of 10 to 50 nm and are preferably added in an amount of 0.1 to 20 mass % to the toner.

As the yellow toner of the present invention, a yellow pigment may be additionally used together with a coloring compound represented by the above general formula (1).

Examples of the yellow pigment usable in the present invention include a monoazo pigment, a disazo pigment, and a polyazo pigment. Among these, the following is preferable: C.I. Pigment Yellow 74, C.I. Pigment Yellow 93, C.I. Pigment Yellow 128, and C.I. Pigment Yellow 155.

A method for producing toner particles is not particularly limited and may be a conventionally used production method. Specific examples thereof include a pulverizing method, a suspension polymerization method, and an emulsion polymerization method. It is preferred to use a coloring compound represented by the above formula (2), causing no inhibition of polymerization, particularly in a method involving polymerization reaction in the process for producing toner particles, such as the suspension polymerization method and emulsion polymerization method.

Any release agent conventionally used for toners may be employed as a release agent. Specific examples thereof include olefins such as low molecular weight polypropylene, low molecular weight polyethylene, an ethylene-propylene copolymer, and wax such as microcrystalline wax, carnauba wax, Sasol wax, and paraffin wax. These release agents are each preferably added to the toner in an amount of 1 to 5 mass % based on the weight of the toner.

A charge control agent may be added as needed; however, it is preferably colorless in view of an influence on color. Examples thereof include quaternary ammonium salts and calixarene.

When a two-component developer having a toner and a magnetic carrier is used, the magnetic carrier may be any of a non-coated carrier composed only of magnetic material particles such as iron-ferrite particles and a resin-coated carrier in which the surfaces of magnetic material particles are coated with resin. The magnetic carrier preferably has a volume-average particle diameter of 30 to 150 μm.

An image-forming method to which the toner of the present invention is applied is not particularly limited. By way of example, the toner of the present invention is applied to a method which involves repeatedly forming a color image on a photosensitive member and then transferring the image to an image formation material such as paper to form an image, or a method which involves successively transferring an image formed on a photosensitive member to an intermediate transfer member to form a color image on the intermediate transfer member and then transferring the image to an image formation material such as paper to form a color image.

The sheet for heat-sensitive transfer recording according to the present invention and the ink used in the sheet for heat-sensitive transfer recording will be described below.

The sheet for heat-sensitive transfer recording according to the present invention includes a substrate and a coloring material layer, wherein the coloring material layer contains a coloring compound represented by the above-described general formula (1). In the sheet for heat-sensitive transfer recording according to the present invention, the coloring compound represented by the above-described general formula (1) may be used in combination with a coloring compound having a different structure, such as a styryl, quinophthalone, methine or pyridone azo structure.

The sheet for heat-sensitive transfer recording according to the present invention can be typically produced by coating a base film as a substrate with an ink prepared by dissolving, or dispersing in fine particle form, the coloring compound together with a binding agent in a medium, followed by drying. However, the sheet of the present invention is not limited to the sheet for heat-sensitive transfer recording prepared by this method.

The binding agent for preparing the ink includes various resins. Among others, the following are preferable: water-soluble resins such as cellulose, acrylic acid, starch and epoxy resins and organic solvent-soluble resins such as acrylic resin, methacrylic resin, polystyrene, polycarbonate, polyethersulfone, polyvinyl butyral, ethyl cellulose, acetyl cellulose, polyester, AS resin and phenoxy resin. These resins may be used singly or in a combination of two or more of them. The mass ratio of the binding agent and the coloring compound used in the ink (binding agent:coloring compound) is suitably in the range of 1:2 to 2:1.

The medium for preparing the ink includes various organic solvents in addition to water. Among others, the following are preferable: alcohols such as methyl alcohol, ethyl alcohol, isopropyl alcohol, and isobutyl alcohol; cellosolves such as methyl cellosolve and ethyl cellosolve; aromatics such as toluene, xylene, and chlorobenzene; esters such as ethyl acetate and butyl acetate; ketones such as acetone, methyl ethyl ketone, methyl isobutyl ketone, and cyclohexanone; chlorinated solvents such as methylene chloride, chloroform, and trichloroethylene; ethers such as tetrahydrofuran and dioxane; N,N-dimethylformamide; and N-methylpyrrolidone. These organic solvents may be used singly or in a mixture of two or more of them.

According to the present invention, additives may be optionally added to the ink, such as organic or inorganic non-sublimation fine particles, a dispersant, an antistatic agent, an antifoaming agent, an antioxidant, and a viscosity modifier.

The base film, the substrate, to be coated with the ink is preferably a thin paper such as a capacitor paper and a glassine paper or a plastic film having good heat resistance, such as polyester, polycarbonate, polyamide, polyimide and polyaramid films. The substrate preferably has a thickness of 3 to 50 μm. Among these base films, a polyethylene terephthalate film is particularly preferable in terms of mechanical strength, solvent resistance, economical efficiency, etc.

In the present invention, it is preferable that a heat-resistant resin layer containing a lubricant, heat-resistant fine particles having high lubricity, a surfactant, a heat-resistant binding agent, etc. is further formed on the face opposite to the coloring material layer of the substrate for the purpose of improving heat resistance and thermal head traveling properties. Examples of the lubricant include an amino-modified silicone compound and a carboxy-modified silicone compound. Examples of the heat-resistant fine particles include fine particles such as silica fine particles. Examples of the binding agent include an acrylic resin.

Methods for coating the base film with the ink include methods using a bar coater, a gravure coater, a reverse roll coating machine, a rod coater, and an air doctor coater. The ink is preferably applied so that the coloring material layer has a thickness of 0.1 to 5 μm after drying.

Infrared light or laser light as well as a thermal head may be further utilized as a means for heating the sheet for heat-sensitive transfer recording according to the present invention. An current-conducting heat generation film that generates heat by sending electricity to the base film itself may also be used as an current-conducting type dye transfer sheet.

It will be appreciated that the coloring compound according to the present invention can be used in the form of an ink applied to other recording methods, for example, ink jet printing, or as a material for common writing utensils. The coloring compound according to the present invention can be not only used in applications as a colorant, but also sufficiently applied to electronic industry materials such as a dye for optical recording and a dye for color filters.

EXAMPLES

The present invention is described below in further detail by way of Examples and Comparative Examples. However, the invention is by no means limited to these Examples. In addition, "parts" and "%" used in the following description are by mass unless otherwise noted.

Example 1

Coloring compounds represented by the above-described general formula (1) were obtained as described below.

Synthesis Example 1

Production of the coloring compound (4) represented by the following formula in which, in the formula (1), $R_1$ represents a 2-ethylhexyl group; $R_2$ represents a hydrogen atom; $R_3$ represents a methyl group; and $R_4$ to $R_7$ each represent a hydrogen atom.

Coloring compound (4)

To 5.0 g of o-nitroaniline, 9 mL of concentrated hydrochloric acid and 50 mL of water were added, which was then stirred under cooling with ice. To this solution, a solution with 2.6 g of sodium nitrite dissolved in 10 mL of water at 5° C. or lower was dropwise added, which was then stirred for one hour. Subsequently, 0.5 g of amidosulfuric acid was added thereto to decompose excess nitrous acid to prepare a diazotized solution.

In addition, 7.7 g of N-(2-ethylhexyl)-3-carbamoyl-4-methyl-6-hydroxypyrid-2-one was dissolved in 100 mL of methanol. This solution was stirred under cooling with ice, to which the above diazotized solution was added dropwise at 5° C. or lower, followed by adding a 25% sodium hydroxide aqueous solution to adjust the pH to 0 to 1. After the reaction was completed, 50 mL of water was added, and methanol was distilled off under reduced pressure, followed by washing the resultant precipitate with water. The precipitate was dried, dissolved in chloroform, and reprecipitated with n-heptane to produce the coloring compound (4) represented by the above formula. NMR analysis, mass spectrometry, HPLC analysis, and UV/Vis spectrometry using the above-described apparatuses, proved that the resultant compound had the above structure of the compound (4). The analysis results are shown below.

(Analyses of Coloring Compound (4))
(1) Results of $^1$H NMR (400 MHz, $CDCl_3$, Room Temperature): δ [ppm]=8.29 (dd, 1H), 8.12 (dd, 1H), 7.73 (dt, 1H), 7.28 (dt, 1H), 7.09 (br, 1H), 6.16 (br, 1H), 3.93 (octet, 2H), 2.59 (s, 3H), 1.81-1.86 (m, 1H), 1.19-1.41 (m, 8H), 0.87-0.94 (m, 6H)
(2) Results of $^{13}$C NMR (100 MHz, $CDCl_3$, Room Temperature): δ [ppm]=166.6, 162.7, 160.7, 151.2, 138.2, 135.9, 135.6, 127.5, 126.1, 124.3, 123.6, 117.5, 43.6, 37.5, 30.4, 28.4, 23.8, 23.0, 15.2, 14.0, 10.5
(3) Results of ESI-TOF MS:
m/z=430.209 $[M+H]^+$
(4) Results of HPLC: purity=96.2 area %, retention time=3.19 minutes [$CH_3OH$—$H_2O$]=9:1 (v/v)]
(5) Results of UV/Vis spectrometry:
$\lambda_{max}$=429 nm, $\epsilon$=31,723 $M^{-1}cm^{-1}$ (solvent: $CH_3OH$, room temperature)

Synthesis Example 2

Production of the coloring compound (5) represented by the following formula in which, in the formula (1), $R_1$ represents a 2-ethylhexyl group; $R_2$ represents a tert-butyl group; $R_3$ represents a methyl group; $R_4$, $R_5$, and $R_7$ each represent a hydrogen atom; and $R_6$ represents a trifluoromethyl group.

Coloring compound (5)

To 15 mL of glacial acetic acid and 5 mL of concentrated sulfuric acid, 5.0 g of N-(2-ethylhexyl)-3-cyano-4-methyl-6-hydroxypyrid-2-one was added under cooling with ice. Thereto, 3.5 g of tert-butanol was dropwise added while keeping the solution temperature at 0 to 5° C. After that, the solution was stirred at 0 to 5° C. for one hour, followed by gradually returning the solution temperature to room temperature. The solution was stirred for 24 hours, then poured into 300 mL of ice water, and extracted with chloroform, followed by washing the organic phase with water. The organic phase was dehydrated with sodium sulfate and the solvent was distilled off under reduced pressure, to thereby obtain N-(2-ethylhexyl)-3-(N-tert-butylcarbamoyl)-4-methyl-6-hydroxypyrid-2-one.

To 3.0 g of o-nitro-p-trifluoromethylaniline, 15 mL of concentrated sulfuric acid was added, which was then stirred under cooling with ice. To this solution, 5.0 g of 40% nitrosylsulfuric acid was dropwise added at 5° C. or lower, which was then stirred for one hour to make a diazotized solution.

In addition, 5.0 g of the N-(2-ethylhexyl)-3-(N-tert-butylcarbamoyl)-4-methyl-6-hydroxypyrid-2-one previously obtained was dissolved in 30 mL of methanol and 30 mL of water, which was then stirred under cooling with ice. To this solution, 0.14 g of amidosulfuric acid was added, to which the above diazotized solution was added dropwise while keeping the solution temperature at 5° C. or lower. After the dropwise addition was completed, a 25% sodium hydroxide aqueous solution was added to adjust the pH to 0 to 1. After the reaction was completed, 50 mL of water was added, and methanol was distilled off under reduced pressure, followed by washing the resultant precipitate with water. The precipitate was dissolved in chloroform and reprecipitated with n-heptane to produce the coloring compound (5) represented by the above formula. NMR analysis, mass spectrometry, HPLC analysis, and UV/Vis spectrometry using the above-described apparatuses, proved that the resultant compound had the above structure of the compound (5). The analysis results are shown below.

(Analyses of Coloring Compound (5))
(1) Results of $^1$H NMR (400 MHz, $CDCl_3$, Room Temperature): δ [ppm]=8.57 (d, 1H), 8.23 (d, 1H), 7.91 (dd, 1H), 6.15 (br, 1H), 3.90 (octet, 2H), 2.44 (s, 3H), 1.83 (m, 1H), 1.49 (s, 9H), 1.23-1.36 (m, 8H), (m, 6H)
(2) Results of $^{13}$C NMR (100 MHz, $CDCl_3$, Room Temperature): δ [ppm]=163.3, 162.2, 160.8, 147.0, 140.9, 134.4, 132.1, 132.0, 129.3, 128.1, 124.0, 123.9, 118.1, 52.3, 43.8, 37.4, 30.4, 28.7, 28.3, 23.7, 23.1, 14.7, 14.0, 10.5
(3) Results of ESI-TOF MS:
m/z=554.260 $[M+H]^+$
(4) Results of HPLC: purity=96.8 area %, retention time=5.42 minutes [$CH_3OH$—$H_2O$]=9:1 (v/v)]
(5) Results of UV/Vis spectrometry:
$\lambda_{max}$=421 nm, $\epsilon$=36,148 $M^{-1}cm^{-1}$ (solvent: $CH_3OH$, room temperature)

Synthesis Example 3

Production of the coloring compound (6) represented by the following formula in which, in the formula (1), $R_1$ represents a 2-ethylhexyl group; $R_2$ represents a hydrogen atom; $R_3$ represents a methyl group; $R_4$, $R_5$, and $R_7$ each represent a hydrogen atom; and $R_6$ represents a fluorine atom.

Coloring compound (6)

To 5.0 g of o-nitro-p-fluoroaniline, 25 mL of concentrated sulfuric acid was added, which was then stirred under cooling with ice. To this solution, 11.2 g of 40% nitrosylsulfuric acid was dropwise added at 5° C. or lower, which was then stirred for one hour to make a diazotized solution.

In addition, 12.6 g of N-(2-ethylhexyl)-3-carbamoyl-4-methyl-6-hydroxypyrid-2-one was dissolved in 100 mL of methanol. To this solution, 0.31 g of amidosulfuric acid was added, to which the above diazotized solution was added dropwise while keeping the solution temperature at 5° C. or lower. After the dropwise addition was completed, a 25% sodium hydroxide aqueous solution was added to adjust the pH to 0 to 1. After the reaction was completed, 50 mL of water was added, and methanol was distilled off under reduced pressure, followed by washing the resultant precipitate with water. The precipitate was dissolved in chloroform and reprecipitated with n-heptane to provide the coloring compound (6) represented by the above formula. NMR analysis, mass spectrometry, HPLC analysis, and UV/Vis spectrometry using the above-described apparatuses, proved that the resultant compound had the above structure of the compound (6). The analysis results are shown below.

(Analyses of Coloring Compound (6))

(1) Results of $^1$H NMR (400 MHz, CDCl$_3$, Room Temperature): δ [ppm]=8.15 (dd, 1H), 8.02 (dd, 1H), 7.52-7.48 (m, 1H), 7.08 (s, 1H), 5.99 (s, 1H), 3.95 (octet, 2H), 2.60 (s, 3H), 1.86-1.79 (m, 1H), 1.39-1.19 (m, 8H), 0.92-0.87 (m, 6H)

(2) Results of $^{13}$C NMR (100 MHz, CDCl$_3$, Room Temperature): δ [ppm]=166.5, 162.7, 160.7, 151.4, 135.0, 124.1, 123.9, 123.5, 119.4, 119.3, 112.7, 112.5, 43.7, 37.5, 30.5, 28.4, 23.8, 23.0, 15.2, 14.1, 10.5

(3) Results of ESI-TOF MS: m/z=448.204 [M+H]$^+$ (4) Results of HPLC: purity=99.7 area %, retention time=3.32 minutes [CH$_3$OH—H$_2$O]=9:1 (v/v)]

(5) Results of UV/Vis spectrometry: $\lambda_{max}$=434 nm, $\epsilon$=59,602 M$^1$ cm$^{-1}$ (solvent: CH$_3$OH, room temperature)

Other Synthesis Examples

According to the methods of Synthesis Examples 1, 2 and 3, synthesis was carried out to give the structures described in Table 1 to produce coloring compounds (4) to (18). The structures of the resultant coloring compounds were confirmed by NMR analysis, mass spectrometry, HPLC analysis, and UV/Vis spectrometry as described for the above-described coloring compounds (4), (5) and (6).

TABLE 1

Coloring compounds (4) to (18)

| Compound No. | $R_1$ | $R_2$ | $R_3$ | $R_4$ | $R_5$ | $R_6$ | $R_7$ | Synthesis Example Applied |
|---|---|---|---|---|---|---|---|---|
| (4) | —CH$_2$CH(C$_2$H$_5$)C$_4$H$_9$ | —H | —CH$_3$ | —H | —H | —H | —H | Synthesis Example 1 |
| (5) | —CH$_2$CH(C$_2$H$_5$)C$_4$H$_9$ | —C(CH$_3$)$_3$ | —CH$_3$ | —H | —H | —CF$_3$ | —H | Synthesis Example 2 |
| (6) | —CH$_2$CH(C$_2$H$_5$)C$_4$H$_9$ | —H | —CH$_3$ | —H | —H | —F | —H | Synthesis Example 3 |
| (7) | —CH$_2$CH(C$_2$H$_5$)C$_4$H$_9$ | —H | —CH$_3$ | —H | —F | —F | —H | Synthesis Example 3 |
| (8) | —CH$_2$CH(C$_2$H$_5$)C$_4$H$_9$ | —H | —CH$_3$ | —F | —F | —F | —H | Synthesis Example 3 |
| (9) | —CH$_2$CH(C$_2$H$_5$)C$_4$H$_9$ | —H | —CH$_3$ | —NO$_2$ | —H | —CF$_3$ | —H | Synthesis Example 3 |
| (10) | —CH$_2$CH(C$_2$H$_5$)C$_4$H$_9$ | —H | —CH$_3$ | —Br | —H | —CF$_3$ | —H | Synthesis Example 3 |
| (11) | —CH$_2$CH(C$_2$H$_5$)C$_4$H$_9$ | —H | —CH$_3$ | —H | —H | —CN | —H | Synthesis Example 3 |
| (12) | —CH$_2$CH(C$_2$H$_5$)C$_4$H$_9$ | —H | —CH$_3$ | —H | —H | —CF$_3$ | —H | Synthesis Example 3 |
| (13) | —C$_2$H$_5$ | —C(CH$_3$)$_3$ | phenyl | —H | —H | —CF$_3$ | —H | Synthesis Example 2 |
| (14) | —H | —C(C$_2$H$_5$)(CH$_3$)C$_4$H$_9$ | —CH$_3$ | —H | —H | —CF$_3$ | —H | Synthesis Example 2 |
| (15) | phenyl | —H | —CH$_3$ | —H | —H | —H | —H | Synthesis Example 1 |

TABLE 1-continued

Coloring compounds (4) to (18)

| Compound No. | R₁ | R₂ | R₃ | R₄ | R₅ | R₆ | R₇ | Synthesis Example Applied |
|---|---|---|---|---|---|---|---|---|
| (16) |  | —H | —CH₃ | —H | —H | —H | —H | Synthesis Example 1 |
| (17) | —CH₂CH(C₂H₅)C₄H₉ | cyclopentyl (—HC(CH₂CH₂CH₂)) | —CH₃ | —H | —H | —H | —H | Synthesis Example 2 |
| (18) | —CH₂CH(C₂H₅)C₄H₉ | —CH₂—C₆H₅ | —CH₃ | —H | —H | —CF₃ | —H | Synthesis Example 2 |

Coloring compounds for comparison were synthesized according to the above Synthesis Examples. The compound of the following structure described in Japanese Patent Application Laid-Open No. 09-111143 was synthesized as comparative compound (1), and the compound of the following structure described in Example 2 of U.K. Patent No. 2032448 specification, as comparative compound (2).

Comparative Compound (1)

Comparative Compound (2)

Example 2

Solubility Check

A solubility test was performed to measure the solubility of a coloring compound in chloroform at room temperature. The solubility was evaluated as described below.
A: 5% or more solubility in chloroform
B: 1% or more and less than 5% solubility in chloroform
C: less than 1% solubility in chloroform
A solubility of 1% or more in chloroform was determined to indicate high compatibility with resin.

<Color Tone Evaluation>

A coloring compound was dissolved in tetrahydrofuran/cyclohexanone (=1/1 (v/v)) to prepare a 0.04 mol/L solution, which was then filtered with a filter (Φ0.2 μm). The prepared coloring compound solution was applied on CLC color copy paper (manufactured by Canon Inc.) by means of an applicator (0.1 mm). Subsequently, a solution in which part of the coloring compound solution was diluted 2-fold was prepared and applied in the same manner. This operation was repeated to prepare a color tone evaluation sample. The sample was then air-dried overnight and analyzed by using SpectroLino (manufactured by Gretag Machbeth). Optical density and chromaticity ($L^*$, $a^*$, $b^*$) were determined on the basis of the $L^*a^*b^*$ color system. Chroma ($c^*$) was calculated according to the following equation on the basis of measurements of the color characteristics.

$$\mathrm{Chroma}(c^*) = \sqrt{\{(a^*)^2 + (b^*)^2\}}$$

The evaluation was performed as below.
For the same $L^*$ value, a larger $c^*$ value can be said to indicate a better color tone. The color tone was evaluated using the value of $c^*$ in $L^*=88$.
A: The $c^*$ value is 80 or more.
B: The $c^*$ value is 75 or more and less than 80.
C: The $c^*$ value is less than 75.
A $c^*$ value of 75 or more in $L^*=88$ was determined to indicate a good color tone.

<Light Resistance Evaluation>

A coloring compound was dissolved in tetrahydrofuran/cyclohexanone (=1/1 (v/v)) to prepare a 0.04 mol/L solution, which was then filtered with a filter (Φ0.2 μm). The prepared coloring compound solution was applied on CLC color copy paper (manufactured by Canon Inc.) by a bar coat method (Bar No. 3) and air-dried overnight. The test paper was then subjected to an irradiation experiment using Sun Tester (XF-180CPS, manufactured by Shimadzu Corporation) under the conditions of an illuminance of 765 w/m$^2$, a temperature of 50° C. and an irradiation time of 20 hours. The test paper before and after irradiation was analyzed by means of SpectroLino (from Gretag Machbeth). Optical density and chromaticity (L*, a*, b*) were determined on the basis of the L*a*b* color system. Color difference (ΔE) was calculated according to the following equation on the basis of measurements of the color characteristics.

Collor Difference $(\Delta E) =$ $$\sqrt{\{(a^*_{After\ Testing} - a^*_{Before\ Testing})^2 + (b^*_{After\ Testing} - b^*_{Before\ Testing})^2 + (L^*_{After\ Testing} - L^*_{Before\ Testing})^2\}}$$

The evaluation was performed as below.

A: The ΔE value is less than 10.

B: The ΔE value is 10 or more and less than 20.

C: The ΔE value is 20 or more.

The ΔE value of less than 20 was determined to indicate good light resistance.

A series of the coloring compounds (4) to (18) and the comparative compounds (1) and (2) were evaluated for solubility, color tone and light resistance. The results are shown in Table 2.

TABLE 2

Evaluation Results of Coloring compounds

| Compound No. | Solubility | Color Tone | Light Resistance |
|---|---|---|---|
| (4) | B | A | A |
| (5) | A | A | A |
| (6) | B | B | A |
| (7) | A | B | B |
| (8) | A | B | B |
| (9) | B | A | B |
| (10) | B | A | A |
| (11) | A | A | A |
| (12) | A | A | A |
| (13) | A | A | B |
| (14) | B | A | A |
| (15) | B | A | A |
| (16) | B | A | A |
| (17) | A | A | B |
| (18) | A | A | B |
| Comparative Compound (1) | B | C | C |
| Comparative Compound (2) | C | B | C |

Table 2 showed that the coloring compounds represented by the general formula (1) according to the present invention have a good color tone because of their large c* values and were superior in light resistance. It was also shown that the coloring compounds in which the number of carbon atoms of $R_1$, $R_2$ and $R_3$ in the general formula (1) was larger tend to have higher solubility in chloroform and therefore was more advantageous in compatibility with resin.

Example 3

Toner Production Example 1

The following materials were mixed in advance, and melt-kneaded with a twin-screw extruder. The kneaded matter was cooled and coarsely ground with a hammer mill. The ground matter was finely pulverized with a jet mill. The resultant pulverized matter was classified to produce yellow toner particles.

| | |
|---|---|
| Polyester Resin (Bisphenol A propylene oxide adduct/bisphenol A ethylene oxide adduct/terephthalic acid derivative; (Tg = 65° C.)) | 100 parts by mass |

-continued

| | |
|---|---|
| Coloring compound (4) | 3 parts by mass |
| C.I. Pigment Yellow 93 | 3 parts by mass |
| Aluminum Salicylate Compound (Bontron E-88 manufactured by Orient Chemical Industries, Ltd.) | 2 parts by mass |
| Paraffin Wax (melting point = 65° C.) | 10 parts by mass |

Using a Henschel mixer (manufactured by Mitsui Mining Co., Ltd.), 100 parts by mass of the above classified powder was dry-mixed with 1.5 parts by mass of silicone oil-treated silica fine powder (BET specific surface area=200 m$^2$/g) to make yellow toner (A).

Toner Production Example 2

Yellow toner (B) was produced in the same manner as in Toner Production Example 1 except that the coloring compound (4) was changed to the coloring compound represented by the above general formula (5).

Toner Production Example 3

Yellow toner (C) was produced in the same manner as in Toner Production Example 1 except that the coloring compound (4) was changed to the above comparative compound (1).

Toner Production Example 4

Yellow toner (D) was produced in the same manner as in Toner Production Example 1 except that the coloring compound (4) was not used and changed to 6 parts by mass of C.I. Pigment Yellow 93.

<Toner Color Tone Evaluation>

Five parts of each of the resultant yellow toners (A) to (D) was mixed with 95 parts of a ferrite carrier coated with acrylic resin to make a developer. Using a modified machine of Color Copier CLC-1100 (manufactured by Canon Inc.; a fixing oil-coating mechanism was omitted), 16-gradation image samples were prepared in which the maximum toner laid-on level was adjusted to 0.45 mg/cmL$^2$ in a normal environment (temperature of 25° C./humidity of 60% RH). In this case, CLC color copy paper (manufactured by Canon Inc.) was used as the base paper for the image samples. The resultant image samples were analyzed by means of SpectroLino (manufactured by Gretag Machbeth). Optical density and chromaticity (L*, a*, b*) were determined on the basis of the L*a*b* color system. Chroma (c*) was calculated according to the following equation on the basis of measurements of the color characteristics.

$$\text{Chroma}(c^*) = \sqrt{\{(a^*)^2 + (b^*)^2\}}$$

For the same L* value, a larger c* value can be said to indicate a better color tone. The color tone was evaluated using the value of c* in L*=91.
A: The c* value is 80 or more.
B: The c* value is 75 or more and less than 80.
C: The c* value is less than 75.
A c* value of 75 or more in L*=91 was determined to indicate a good color tone as yellow toners.

<Toner Light Resistance Evaluation>

The 16-gradation image samples obtained above were subjected to an irradiation test under the condition of an irradiation time of 100 hours using Atlas Weather-Ometer (Ci4000 from Toyo Seiki Seisaku-Sho Ltd.). The measurement conditions in this case were set to be as follows: black panel: 50° C., chamber: 40° C., rel. humidity: 70%, and irradiance (@340 nm): 0.39 W/m². The test paper before and after irradiation was analyzed by means of SpectroLino (manufactured by Gretag Machbeth). Optical density and chromaticity (L*, a*, b*) were determined on the basis of the L*a*b* color system. Color difference (ΔE) was calculated according to the following equation on the basis of measurements of the color characteristics.

Collor Difference (ΔE) =

$$\sqrt{\{(a^*_{After\ Testing} - a^*_{Before\ Testing})^2 + (b^*_{After\ Testing} - b^*_{Before\ Testing})^2 + (L^*_{After\ Testing} - L^*_{Before\ Testing})^2\}}$$

The evaluation was performed as below.
A: The ΔE value is less than 15.
B: The ΔE value is 15 or more and less than 25.
C: The ΔE value is 25 or more.
A ΔE of less than 25 was determined to indicate good light resistance.

The color tone and light resistance of the yellow toners (A) to (d) were evaluated. The results are shown in Table 3.

TABLE 3

Evaluation Results of Toners

| Toner No. | Coloring Material | Color Tone | Light Resistance |
|---|---|---|---|
| (A) | Coloring compound (4) 3 parts by mass<br>C.I. Pigment Yellow 93<br>3 parts by mass | A | A |
| (B) | Coloring compound (5) 3 parts by mass<br>C.I. Pigment Yellow 93<br>3 parts by mass | A | A |
| (C) | Comparative Compound(1)<br>3 parts by mass<br>C.I. Pigment Yellow 93<br>3 parts by mass | B | C |
| (D) | C.I. Pigment Yellow 93<br>6 parts by mass | C | A |

Table 3 demonstrated that the coloring compounds of the present invention were useful as colorants for yellow toners since the yellow toners using the coloring compounds of the present invention were good in color tone and light resistance.

Example 4

Production Example 1 for Heat-Sensitive Transfer Recording Sheet

The following materials were mixed in advance to prepare ink (A).

| | |
|---|---|
| Polyvinyl Butyral Resin<br>(Denka 3000-K, from Denki Kagaku Kogyo K.K.) | 5 parts by mass |
| Coloring compound (4) | 5 parts by mass |
| Methyl Ethyl Ketone | 45 parts by mass |
| Toluene | 45 parts by mass |

The above ink (A) was applied on a 4.5 μm-thick polyethylene terephthalate film (Lumiler from Toray Industries, Inc.) so as to provide a thickness of 1 μm after drying, and then dried to prepare a heat-sensitive transfer recording sheet (A).

Production Example 2 for Heat-Sensitive Transfer Recording Sheet

An ink (B) was prepared in the same way as in Production Example 1 for Heat-sensitive Transfer Recording Sheet except that the coloring compound (4) was changed to the coloring compound (5). In addition, a heat-sensitive transfer recording sheet (B) was obtained in the same way as in Production Example 1 for Heat-sensitive Transfer Recording Sheet except that the ink (B) was used.

Production Example 3 for Heat-Sensitive Transfer Recording Sheet

An ink (C) was prepared in the same way as in Production Example 1 for Heat-sensitive Transfer Recording Sheet except that the coloring compound (4) was changed to the comparative compound (1). In addition, a heat-sensitive transfer recording sheet (C) was obtained in the same way as in Production Example 1 for Heat-sensitive Transfer Recording Sheet except that the ink (C) was used.

Production Example 4 for Heat-Sensitive Transfer Recording Sheet

An ink (D) was prepared in the same way as in Production Example 1 for Heat-sensitive Transfer Recording Sheet except that the coloring compound (4) was changed to C.I. Disperse Yellow 201. In addition, a heat-sensitive transfer recording sheet (D) was obtained in the same way as in Production Example 1 for Heat-sensitive Transfer Recording Sheet except that the ink (D) was used.

<Color Tone Evaluation of Transferred Image>

The heat-sensitive transfer recording sheets (A) to (D) thus prepared were each cut and attached to the "yellow" section of an ink cassette for CP710 (manufactured by Canon Inc.), and using SELPHY CP710 (manufactured by Canon Inc.), imaged were formed on dedicated printing paper. The formed images were yellow single color solid images and designated as transferred images (A) to (D), respectively. For each transferred image, chromaticity (L*, a*, b*) was determined on the basis of the L*a*b* color system using SpectroLino (manufactured by Gretag Machbeth). Chroma (c*) was calculated according to the following equation on the basis of measurements of the color characteristics.

$$\text{Chroma}(c^*) = \sqrt{\{(a^*)^2 + (b^*)^2\}}$$

The evaluation was performed as below. For the same L* value, a larger c* value can be said to indicate a better color tone. The value of c* is a value in L*=88.
A: The c* value is 80 or more.
B: The c* value is 75 or more and less than 80.
C: The c* value is less than 75.
A c* value of 75 or more in L*=88 was determined to indicate a good color tone.

<Light Resistance Evaluation of Transferred Image>

The resultant transferred images were each subjected to an irradiation test under the condition of an irradiation time of 100 hours using Atlas Weather-Ometer (Ci4000 from Toyo Seiki Seisaku-Sho Ltd.). The measurement conditions in this case were set to be as follows: black panel: 50° C., chamber: 40° C., rel. humidity: 70%, and irradiance (@340 nm): 0.39 W/m². For each transferred image before and after irradiation, chromaticity (L*, a*, b*) was determined based on the L*a*b* color system by using SpectroLino (manufactured by Gretag Machbeth). Color difference (ΔE) was calculated according to the following equation on the basis of measurements of the color characteristics.

Collor Difference (ΔE) =

$$\sqrt{\{(a^*_{\text{After Testing}} - a^*_{\text{Before Testing}})^2 + (b^*_{\text{After Testing}} - b^*_{\text{Before Testing}})^2 + (L^*_{\text{After Testing}} - L^*_{\text{Before Testing}})^2\}}$$

The evaluation was performed as below. A smaller ΔE was determined to indicate more excellent light resistance.
A: The ΔE value is less than 15.
B: The ΔE value is 15 or more and less than 25.
C: The ΔE value is 25 or more.
A ΔE of less than 25 was determined as indicating good light resistance.

The evaluation results of the color tone and light resistance of the transferred images (A) to (D) are shown in Table 4.

TABLE 4

Evaluation Results of Transferred Images

| Transferred Image No. | Coloring Material | Color Tone | Light Resistance |
|---|---|---|---|
| (A) | Coloring compound (4) 5 parts by mass | A | A |
| (B) | Coloring compound (5) 5 parts by mass | A | A |
| (C) | Comparative Compound (1) 5 parts by mass | C | C |
| (D) | C.I. Disperse Yellow 201 5 parts by mass | A | C |

Table 4 demonstrates that the coloring compounds of the present invention were useful as coloring materials for heat-sensitive transfer recording sheets since the transferred images printed with the heat-sensitive transfer recording sheets using the coloring compounds of the present invention were good in color tone and light resistance.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priority to Japanese Patent Application No. 2007-070494, filed Mar. 19, 2007, the disclosure of which is hereby incorporated by reference as part of the present application.

What is claimed is:

1. A coloring compound having a structure represented by the general formula (1):

General Formula (1)

wherein $R_1$ represents a hydrogen atom, an optionally substituted alkyl group, an optionally substituted aryl group, or an optionally substituted aralkyl group; $R_2$ represents a hydrogen atom, an optionally substituted alkyl group, an optionally substituted cycloalkyl group, or an optionally substituted aralkyl group; $R_3$ represents an optionally substituted alkyl group or an optionally substituted aryl group; the total number of carbon atoms of $R_1$, $R_2$ and $R_3$ is 4 or more but 16 or less; $R_4$, $R_5$ and $R_7$ each independently represent a hydrogen atom, a halogen atom or a nitro group; and $R_6$ represents a fluorine atom, a trifluoromethyl group, or a cyano group.

2. The coloring compound according to claim 1, wherein at least one of $R_1$, $R_2$ and $R_3$ in the general formula (1) represents a substituent having 4 or more carbons.

3. The coloring compound according to claim 1, wherein $R_3$ in the general formula (1) represents a methyl group or a phenyl group.

4. A yellow toner comprising yellow toner particles having at least a binder resin and a colorant, wherein the colorant comprises the coloring compound according to claim 1.

5. The yellow toner according to claim 4, wherein the colorant further comprises a yellow pigment.

6. A sheet for heat-sensitive transfer recording comprising a substrate and a coloring material layer containing the coloring compound according to claim 1 on the substrate.

7. An ink comprising the coloring compound according to claim 1.

* * * * *